(12) United States Patent
King et al.

(10) Patent No.: US 10,835,114 B2
(45) Date of Patent: Nov. 17, 2020

(54) POINT OF USE CLEANING SYSTEM FOR ENDOSCOPES

(71) Applicant: One Surgical, Inc., Memphis, TN (US)

(72) Inventors: Steven M. King, Memphis, TN (US); Shawn Flynn, Memphis, TN (US)

(73) Assignee: One Surgical, Inc., Memphis, TN (US)

( * ) Notice: Subject to any disclaimer, the term of this patent is extended or adjusted under 35 U.S.C. 154(b) by 275 days.

(21) Appl. No.: 15/436,181

(22) Filed: Feb. 17, 2017

(65) Prior Publication Data

US 2017/0296046 A1    Oct. 19, 2017

Related U.S. Application Data

(60) Provisional application No. 62/296,649, filed on Feb. 18, 2016.

(51) Int. Cl.
*A61B 1/12* (2006.01)
*B08B 9/032* (2006.01)

(52) U.S. Cl.
CPC ............ *A61B 1/125* (2013.01); *B08B 9/0321* (2013.01)

(58) Field of Classification Search
None
See application file for complete search history.

(56) References Cited

U.S. PATENT DOCUMENTS 5,755,894 A * 5/1998 Bowman ................. A61B 1/121
134/166 C
2008/0251102 A1* 10/2008 Haack ....................... B08B 1/00
134/6

FOREIGN PATENT DOCUMENTS

EP              2060276 A1 *  5/2009  ............. A61B 1/123

\* cited by examiner

*Primary Examiner* — Rita P Adhlakha

(57) ABSTRACT

The invention includes devices, arrangements and methods for treating an endoscope after use to prevent adhesion of bioburden on internal walls of a lumen of the endoscope. After treatment, the device is stored in the treated condition until cleaning. The device is configured to selectively deliver cleaning solution to the endoscope. The device can be a circulating embodiment having a pump. A filter can be provided to filter debris during circulation. The device can be a non-circulating embodiment having a hydrophobic filter for release of air. Fittings are provided on the device components to selectively attach the device to endoscopes.

4 Claims, 6 Drawing Sheets

POINT OF USE CLEANING SYSTEM FOR ENDOSCOPES

CROSS REFERENCE TO RELATED APPLICATIONS

This application claims priority to and incorporates by reference the entirety of the following: U.S. Provisional Patent Application 62/296,649, filed Feb. 18, 2016.

STATEMENT REGARDING FEDERALLY SPONSORED RESEARCH

Not applicable

FIELD OF THE INVENTION

The present invention relates to cleaning of hospital equipment, and more particularly to the cleaning of endoscopes for preparation for reuse with patients.

BACKGROUND OF THE INVENTION

An endoscope is a flexible device with a camera and, a light source, and a lens system for transmitting images from the camera to an eyepiece or a display monitor. Physicians use endoscopes to look inside of patients' bodies for medical reasons, such as to investigate symptoms, confirm a diagnosis, or administer a treatment. Unlike most other medical imaging techniques, endoscopes are inserted directly into the body.

Endoscopes are expensive (e.g. $70,000 per instrument) and are therefore designed for re-use. After a scope is used on a patient, it must be pre-cleaned, high-level disinfected and in some cases sterilized before being used on a subsequent patient. This procedure is commonly known as reprocessing. Numerous protocols and procedures have been developed for cleaning and sterilizing endoscopes. A typical conventional procedure includes the following:

1. Scope is used in a surgical procedure
2. Scope is pre-cleaned at the point of use
3. Scope is collected for reprocessing
4. Scope is transported to a cleaning and sterilization facility (typically located in the hospital where the scope was used)
5. Scope is leak tested
6. Scope is manually cleaned
7. Scope is high-level disinfected or
8. Scope is sterilized
9. Scope is inspected for integrity, function and cleanliness
10. Scope is stored to prevent damage and re-contamination
11. Scope is returned to a surgical site for use in surgery A delay sometimes takes place between steps 2, 3 and 4. After use, an endoscope often retains fluids and tissues from the patient, which can be referred to as "bio-burden. Delay allows bio-burden inside of the scope to dry out. Once dried, bio-burden inside the scope can be difficult to remove in step 6 (manual cleaning). Bio-burden inside the scope can retain bacteria and viruses. Currently, a particularly dangerous bacteria is CRE. CRE is antibiotic resistant and kills about 40 percent of patients who become infected with it. CRE and other infectious agents have been inadvertently transmitted from one patient to another through contaminated endoscopes. In some cases, patients have died of infection caused by contaminated scopes.

There is thus a need for improved apparatus and methods cleaning endoscopes.

OBJECTS AND SUMMARY OF THE INVENTION

It is an object of the invention to provide devices and methods for treating endoscopes immediately or shortly after use to prevent adherence of bioburden to internal lumen of endoscopes.

It is another object of the invention to provide devices and methods for treating endoscopes immediately or shortly after use that is easy and economical to use in a hospital setting.

It is yet another object of the invention to provide devices and methods for treating endoscopes immediately or shortly after use that minimizes or prevents infection of endoscopes by microorganisms.

The foregoing objectives are achieved by providing devices, arrangements and methods having the features described herein.

The invention includes a device for treating an endoscope after use to prevent adhesion of bioburden on internal walls of a lumen of the endoscope. The device comprises at least one endoscope input member, a trailing end of the at least one endoscope input member configured to selectively attach to at least one of the input ports of the endoscope. The device includes an endoscope outlet member, a leading end of the endoscope outlet member configured to selectively attach to the distal end of the endoscope insertion tube. A cleaning solution is provided. A pump is situated for use in selective circulation of the cleaning solution through the endoscope input member, through the lumen of the endoscope, through the endoscope outlet member, and back into the lumen of the endoscope via the endoscope input member.

The device preferably includes a reservoir, the reservoir configured for storing and retaining the cleaning solution until circulation of the cleaning solution in the device. A leading end of the endoscope input member is in fluid communication with the reservoir. A filter can be situated for filtering debris from the enzymatic fluid during circulation of the enzymatic fluid in the device. The filter can be in the reservoir, such that the filter is situated for filtering debris from the enzymatic fluid during circulation of the enzymatic fluid in the device.

An endoscope containment bag is preferably included, the bag sized and configured to receive the endoscope, to thereby protect the endoscope and prevent spilling of the cleaning solution during treatment of the endoscope. The endoscope containment bag can be selectively sealable. The pump can be an electromechanical pump. The pump can be powered by a battery. The pump can be a hand pump. The cleaning solution is preferably an enzymatic cleaning solution.

A filter is preferably provided, the filter situated for filtering debris from the cleaning solution during circulation of the enzymatic fluid in the device. The filter can be contained in the reservoir. An endoscope containment bag is preferably included in the arrangement, the bag sized and configured to receive the endoscope, to thereby protect the endoscope and prevent spilling of the cleaning solution during treatment of the endoscope.

In another embodiment, the device of the invention is a non-circulating device for treating an endoscope after use to prevent adhesion of bioburden on internal walls of a lumen of the endoscope. The device includes an endoscope containment bag sized and configured to receive the endoscope, the containment bag having a reservoir formed therein, a cleaning solution in the reservoir, and the reservoir configured for storing and retaining the cleaning solution until delivery to the endoscope. At least one endoscope input member extends from the reservoir, a trailing end of the at least one endoscope input member configured to selectively attach to at least one of the input ports of the endoscope. The arrangement includes a distal end plug having an input connector on a leading end and a hydrophobic filter on a trailing end. The input connector is configured to selectively attach to the distal end of the endoscope insertion tube. The hydrophobic filter is configured to allow air to escape through the hydrophobic filter while retaining cleaning solution. The reservoir is configured for use in selective delivery of the cleaning solution through the endoscope input member and through the lumen of the endoscope, whereby the distal end plug allows escape of air through the hydrophobic filter during delivery while retaining the fluid in the endoscope. The cleaning solution is preferably an enzymatic cleaning solution. The distal end plug can include a hose section between the input connector and the hydrophobic filter. The hose section can be sufficiently transparent to allow verification of delivery of cleaning solution through the endoscope.

Methods of treating an endoscope to prevent adhesion of bioburden on internal walls of a lumen of the endoscope are provided. In a method of the invention, shortly after use of the endoscope in a medical procedure, a cleaning solution is injected in the endoscope. The cleaning solution is circulated in the endoscope, whereby circulation of the cleaning solution within the endoscope comprises a treated condition in which the enzymatic fluid prevents adhesion of bioburden on the internal walls of the lumen of the endoscope. The endoscope is stored in the treated condition until cleaning of the endoscope. The treated condition is eventually terminated and the scope is cleaned for reuse, such that the treated condition facilitates the cleaning of the endoscope. Other methods of use are provided.

The foregoing and other objects, features, aspects and advantages of the invention will become more apparent from the following detailed description of the invention when considered in conjunction with the accompanying drawings.

PREFERRED EMBODIMENTS OF THE INVENTION

Figure 1:
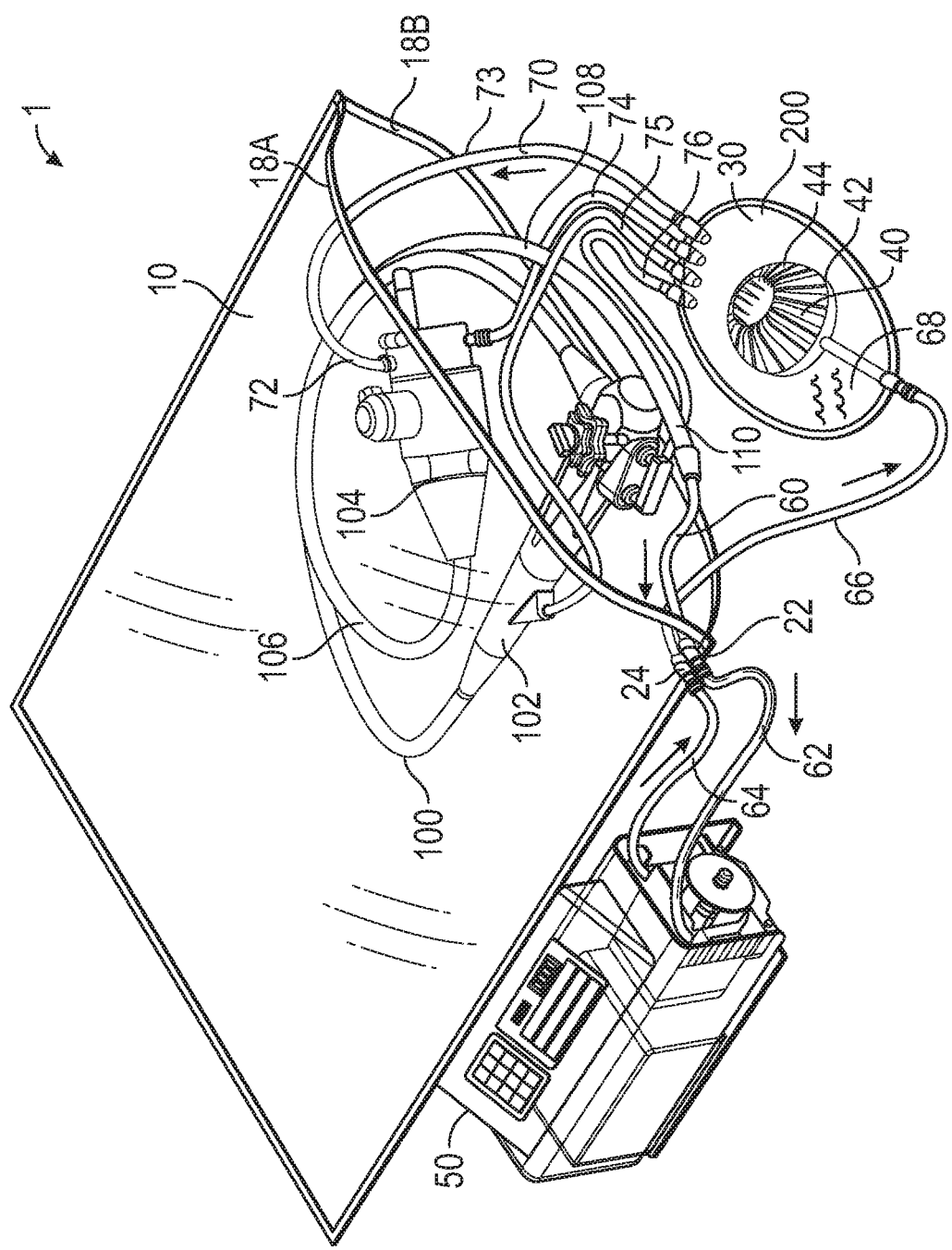
FIG. 1 is a front-side perspective view of one preferred embodiment of an apparatus arrangement of the invention, featuring an electromechanical pump and a reservoir housing a filter.
Figure 2:
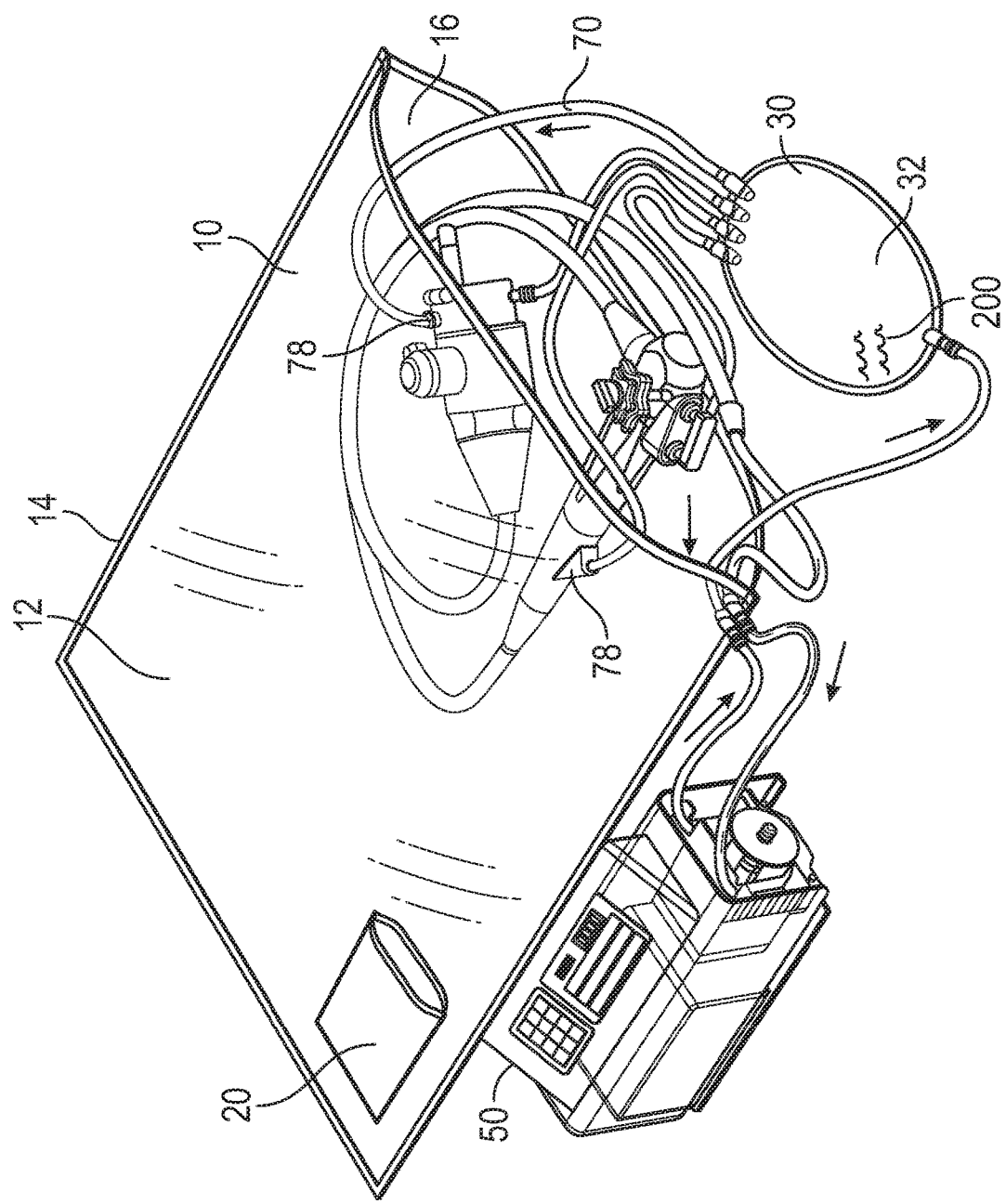
FIG. 2 is a front-side perspective view of one preferred embodiment of an apparatus arrangement of the invention, featuring an electromechanical pump and a reservoir for cleaning fluid.

In the following detailed description of the preferred embodiments, reference is made to the accompanying drawings which form a part hereof, and in which are shown by way of illustration specific embodiments in which the invention may be practiced. It is to be understood that other embodiments may be utilized and structural changes may be made without departing from the scope of the present invention.

The invention provides systems and methods for point-of-contact cleaning of endoscopes. The invention 1 is designed for use with conventional endoscopes 100, such as the endoscope 100 shown in FIG. 1. An endoscope 100 typically includes a control body 102, a light guide connector 104 for providing a light source, and a light guide tube 106 interconnecting the control body 102 and the light guide connector 104. An insertion tube 108 extends from the control body 102. A distal end 110 of the insertion guide is configured for insertion into patients for use in viewing internal tissues of the patient. An endoscope 100 has one or more input ports leading to internal lumen of the endoscope 100. As discussed above, after use in a patient, walls of the endoscope are prone to adhesion of bioburden, which, if not removed, can lead to the propagation of infectious agents within the lumen of the scope. While the invention 1 is designed particularly for solving the problem of infectious agents in flexible endoscopes 100, it can be adapted for use in rigid endoscopes 100. The invention 1 can also be used with other hospital instruments that require cleaning of internal lumen.

Embodiments of devices for treating an endoscope 100 immediately after use to prevent adhesion of bioburden on internal walls of a lumen of the endoscope 100 will now be described. As shown in FIG. 1, the apparatus of the invention 1 comprises, generally, a reservoir 30 for containing cleaning solution 200, a pump 50 device for delivering enzymatic fluid 200, and tubing or other fluid communication means for interconnecting the foregoing components and delivering and circulating cleaning solution in an endoscope 100. A filter 40 can be provided for filtering particulate matter from the cleaning solution 200 during circulation. An endoscope containment bag 10 is preferably provided for use in protecting the endoscope 10, containing leakage of cleaning solution 200, and facilitating set up of the arrangement of the apparatus 1.

In the context of the invention 1, the term "immediately after use" means sufficiently soon after use in a patient such that the introduction of cleaning solution 200 into the lumen of the endoscope 100 substantially prevents the adhesion of bioburden on the walls of the lumen of the endoscope 100. Ideally, the apparatus of the invention 1 will be attached to the endoscope 100 immediately after use of the endoscope 100 in the patient, such as within five minutes after the endoscope 100 has been removed from the patient. However, it is anticipated that the realities of differences in hospital practices and demands on the labor of hospital personnel will result in situations in which "immediately after use" extends beyond five minutes and perhaps to 60 minutes or even more. As time goes on after a procedure and bioburden starts to dry out, the risk of bioburden adhering to the walls of the endoscope 100 increases, but further research will be needed to determine risk levels over time.

In one embodiment, the apparatus includes at least one endoscope input member 70. As shown in FIG. 1, the device can include a plurality of endoscope input members 73 74 75 76 for use in delivering cleaning solution to multiple input ports of the endoscope 100. The endoscope input members 70 are typically flexible tubes, although other structures or combinations of structures could be used, provided that the input member 70 serves to deliver cleaning solution 200 to the endoscope 100. A trailing end 72 of the at least one endoscope input member 70 is configured for selective attachment to at least one of the input ports of the endoscope 100.

Connectors 78 are provided on each of the trailing ends of the various endoscope input members 73 74 75, 76. The connectors 78 selectively attach on to the fluid pathway fitments of the endoscope 100. The connectors 78 can be specialty custom machined fittings or elastomeric connectors that are configured to selectively attach to the endoscope's 100 fluid pathway fitments. Since endoscopes 200 have various designs and fitments, it may be necessary to provide interchangeable connectors 78 that can be placed on the input members 73 74 75, 76 as needed to accommodate different scope designs.

As indicated in FIG. 1, the apparatus further includes an endoscope outlet member 60. A lead end of the endoscope outlet member is 60 configured to selectively attach to the distal end 110 of the endoscope insertion tube 108. During circulation of cleaning solution 200 in the apparatus of the invention 1, the outlet member channels cleaning solution 200 discharged from the endoscope insertion tube 108. The tube set connector for the distal end of the endoscope 100 (discharge end) is designed to be a universal fit elastomeric component that not only provides a secure leak proof connection but also covers and protects the most delicate, expensive part of the scopes.

A cleansing solution 200 is used with the apparatus 1. In one embodiment, the cleansing solution 200 is included as part of the apparatus 1, for ease of use in the pre-cleaning stage. Alternatively, the cleaning solution 200 can be introduced into the apparatus 1 at the time of use. The cleaning solution 200 is preferably an enzymatic cleaning solution 200, which preferably includes proteolytic enzymes for breaking down residual bio-proteins into smaller molecules to prevent bio-burden from attaching to the walls of the internal lumen of the endoscope 100. The inventors contemplate using conventional enzymatic fluids that are readily available on the market. It is anticipated that between about 20 to about 40 ccs of cleaning solution 200 will be used per treatment procedure.

In some embodiments, the apparatus 1 includes a pump 50 for circulating cleaning solution 200. In the embodiment shown in FIG. 1, the pump 50 circulates the cleaning solution through the apparatus 1 such as when the arrangement is connected to an endoscope 100. The pump 50 is situated for use in selective circulation of the cleansing solution 200 through the endoscope input member 70, through the lumen of the endoscope 100, through the endoscope outlet member 60, and back into the lumen of the endoscope 100 via the endoscope input member 70. The pump 50 can be an electromechanical pump, which can be powered by a conventional AC wall outlet, a battery, or like electrical power sources.

Figure 3:
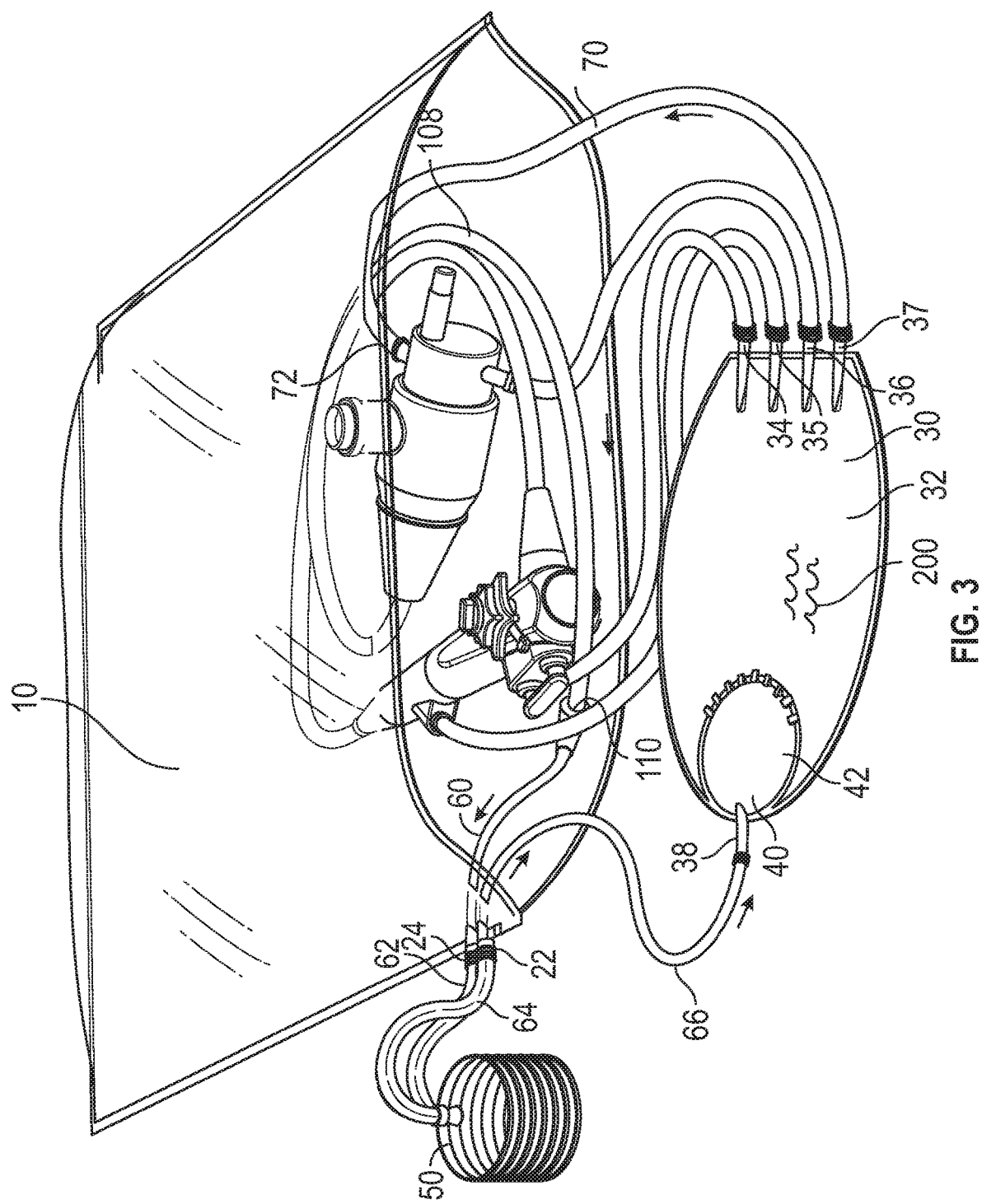
FIG. 3 is a front-side perspective view of one preferred embodiment of an apparatus arrangement of the invention, featuring a hand pump and a reservoir housing a filter.
Figure 4:
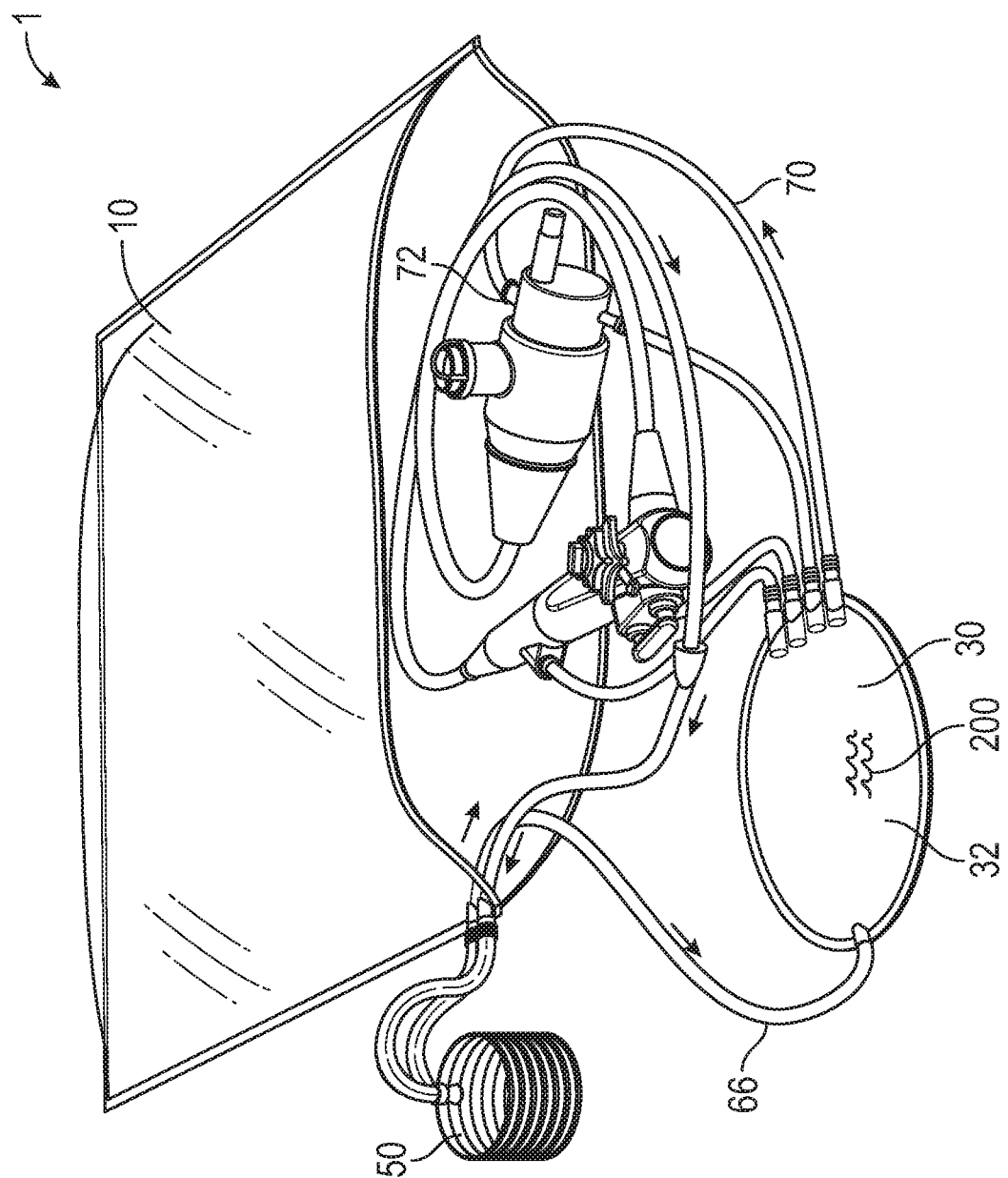
FIG. 4 is a front-side perspective view of one preferred embodiment of an apparatus arrangement of the invention, featuring a hand pump and a reservoir for cleaning fluid.

As shown in FIGS. 3-4, the pump 50 can be a hand pump. The hand pump 50 is configured to be squeezed by hand to circulate cleaning solution 200 through the endoscope 100. It is contemplated that a hand pump 50 would be used as an economical means of providing the functionality of the invention 1.

In the embodiment of FIG. 1, the pump includes a reusable motor assembly. An on-off switch is provided for the motor or flow control. Cycle selections can be provided. A display can be provided to show flow power level (e.g. flow level 1, 2, 3 etc.), running time, battery status, flow history, and the like. A programmable micro control module can be used to optimize flow conditions (e.g. constant flow at low rates; intermittent flow, e.g. on for 10 minutes followed by off selectable to 10 to 120 minutes; Ramp up and down flow rate over time; pulsatile flow to generate high shear to dislodge soften debris). The reusable motor assembly is sealed for easy cleaning. Options for providing motive force for circulating liquid 200 through the scope include: reusable peristaltic pump for pulsatile flow; water pick like pulsatile; centrifugal disposable pump head; disposable electric pump for prime and limited circulation; hand operated pump; crank; bellows; air pot type, and the like. Power sources include conventional wall outlet, disposable battery, rechargeable battery, and the like. The rechargeable battery can be wirelessly charged or through inductive connectivity with a power supply. A backup battery power source can be included to ensure that circulation continues while endoscope is being transported to the cleaning facility.

The device 50 can be configured with processors so that data can be pulled from the pump 50, such as circulation time, volume of fluid circulated etc. The data can be recorded in order to demonstrate that the endoscope 100 has been properly treated prior to the steps of washing and sterilization.

The device preferably includes a reservoir 30. The reservoir is configured for storing and retaining the cleansing solution 200 until circulation of the cleansing solution 200 in the device. In the embodiment of FIG. 1, a leading end 71 of the endoscope input member 70 is in fluid communication with the reservoir 30, such as by attachment to the reservoir 30. In the embodiment shown in FIGS. 1-4, the reservoir can be considered a manifold, since it distributes cleaning solution 200 through multiple outlet ports 34 35 36 37.

While the reservoir can take various forms, it is anticipated that the bag embodiments shown in FIGS. 1-4 will be economical and effective. The reservoir 30 is preferably prefilled with cleaning solution 200 and is sealed shut. No measuring or mixing is required, such that the device 1 is ready to use and can be simply connected to the endoscope 100.

Sealing elements can be provided in the interconnecting tubing and manifold outlet ports to keep liquid in the reservoir 30 until the time of use. The sealing elements can be frangible elements that are broken or activated before the cycle begins in order to open the flow paths. For example, the frangible elements can be of sufficient strength to retain the cleaning solution but weak enough to break once circulation pressure is applied such as by turning on the pump. Alternatively, a valve can be used to open the ports. The valve can be a self-contained piercing pin which creates a fluid passageway (hole) through a laminated foil/poly/heat seal layer film structure which seals all inlet and outlet ports. The pin can be hollow and connected to bellows like structure to allow translational movement of the pin through the sealing membranes in a closed system. The pins could have a lockout or safety that has to be released before pins can moved to pierce the seal. This prevents accidental or premature release of the cleaning solution 200 from the reservoir 30.

In one embodiment, the reservoir 30 has a fill opening so that the reservoir 30 can be filled with a cleaning solution 200 and sealed shut. The user can thus elect to fill the reservoir 30 immediately prior to hook up to an endoscope 100. In other embodiments, the reservoir 30 is prefilled with cleaning solution 200 and disposed of after use.

The device preferably includes a filter 40 situated for filtering debris from the enzymatic fluid 200 during circulation of the enzymatic fluid 200 in the device. Liquid filter 40 will remove debris in fluid that is passing through the scope and prevents lose particulate to re-contaminate the scope lumens of the endoscope 100. In the embodiment of FIG. 1, the filter apparatus 40 is in the reservoir 30, such that the filter apparatus 40 is situated for filtering debris from the enzymatic fluid 200 during circulation of the enzymatic fluid 200 in the device.

The filter 40 is preferably a fluid filter. The filter 40 can be stand alone, housed in the reservoir 30 or integrated into the containment bag 10 for receiving the scope. The filter 40 and the fluid reservoir/manifold 30 can be incorporated into the bottom film layer so film forms one surface of fluid path.

The filter 40 can include a liquid filter media 44. The liquid filter media 44 may be a needle punched nonwoven felt or similar construction with a 20 μm or smaller rating. The liquid filter media 44 can be fine pore mesh or membrane material. The filter media 44 can be enclosed or contained in a filter sock 42. In the embodiment shown in FIG. 1, the filter sock 42 is inside the filter housing 30 and fits over and fastens to the reservoir inlet tube 38 extending into the reservoir 30.

The reservoir 30, liquid filter housing 42, and scope bag 10 are preferably made of sheet vinyl similar to blood bag material. The seams are preferably radiofrequency (RF) sealed. If the reservoir 30 is pre-filled with cleaning solution, the film material used to create the chamber 32 of the reservoir 30 is a high barrier film in order to minimize evaporation through the film.

An air eliminating filter is preferably provided as part of fluid circuit to vent out all or substantially all air in the scope 100 and the interconnecting tubing. The air eliminating filter is preferably located at the connection to the distal end 110 of the scope 100 or is incorporated into the reservoir/manifold 30.

In some embodiments, a loading valve or other resealable opening may be provided to the reservoir 30 for use in introducing enzymatic fluid 200 into the circulation apparatus.

The device preferably includes an endoscope containment bag 10. The endoscope containment bag 10 is sized and configured to receive an endoscope 100, to thereby protect the endoscope and prevent spilling of the cleansing solution 200 during treatment of the endoscope 100. The endoscope containment bag 10 is preferably selectively sealable, such as by a zip-lock mechanism 18A 18B, zipper, snaps, buttons, hook-and-loop (VELCRO®) fastener, or like fastening means.

As shown in FIGS. 1-4, the endoscope containment bag 10 can also be provided with structures for assisting in setting up the arrangement of the apparatus 1. For example, in FIGS. 1-4, an outlet connector 22 and an inlet connector 24 are provided on the bag 10. The outlet connector 22 serves to interconnect the endoscope outlet member 60 with a bag outlet tube 62 in fluid communication. The inlet connector 24 serves to interconnect a bag input member 64 with a reservoir input tube 66 in fluid communication. As can be appreciated from FIGS. 1-4 with the bag outlet and inlet tubes 62 64 operably connected to the pump 50, the arrangement assists in the circulation of cleaning solution 200 through the endoscope. In the embodiment of FIGS. 1-4, the outlet and inlet connectors 22 24 are conveniently located on the side seam of the bag 10 adjacent the opening of the bag 10, but other locations could be used.

The containment bag 10 can be a heavy gauge clear flexible vinyl that is radiofrequency (RF) or heat sealed. A sealing means 18, such as an interlocking seal 18A 18B e.g. a ZIPLOCK® type of arrangement), can be provided along the opening. Other types of high reliability seals that ensure containment of dirty scopes through all post closure activities and actions can be used.

A documentation pouch 20 can be provided on the top surface of the containment bag 10. The documentation pouch 20 can store various forms of information, such as patient information or endoscope cleaning records.

Non-Circulating Embodiments

While it is contemplated that a circulating and preferably continuous flow of cleaning solution 200 will yield ideal results, cost considerations may lead to use of simplified systems in some hospital settings. To that end, non-circulating embodiments of the invention 1 will now be described.

Figure 5:
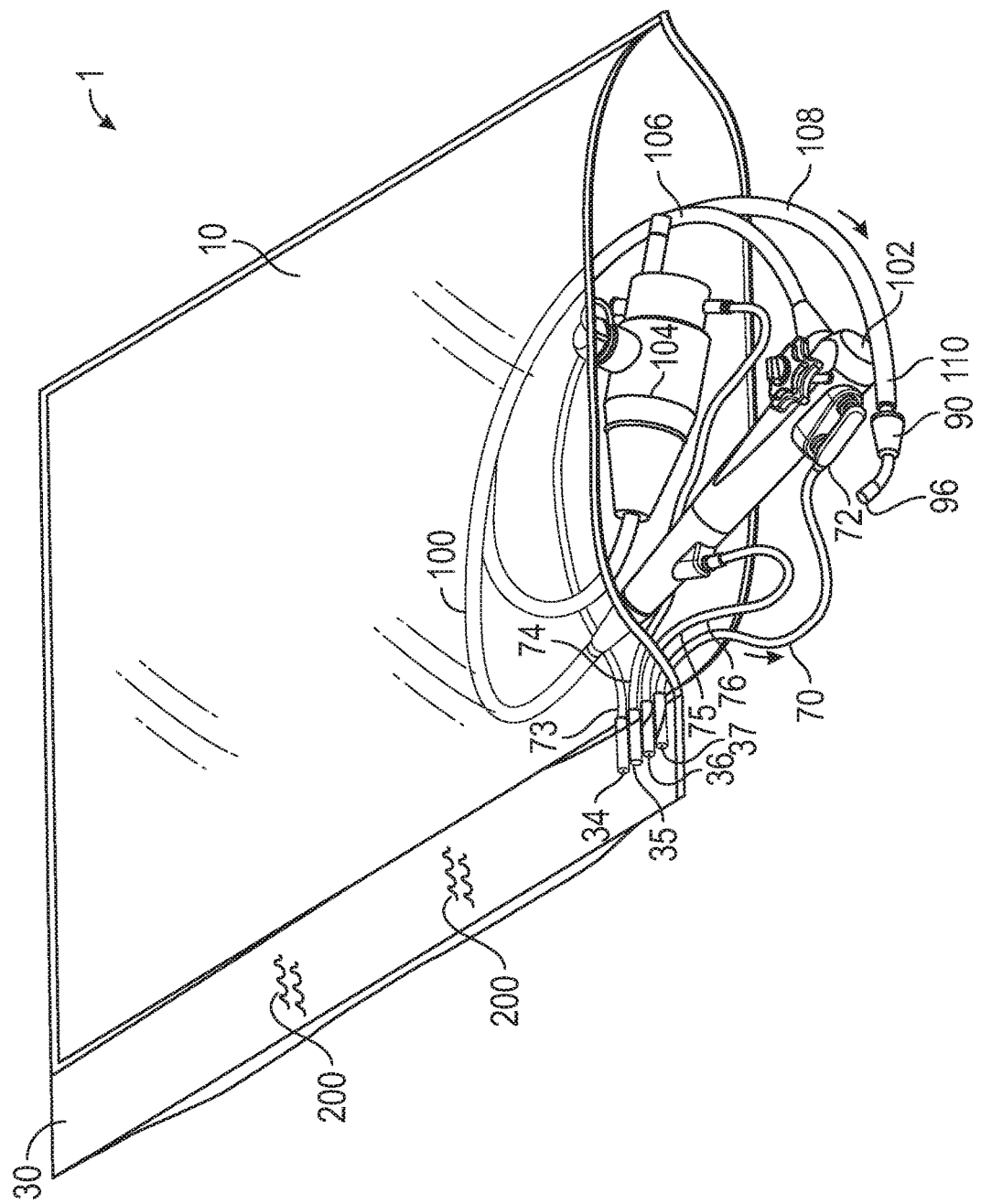
FIG. 5 is a front-side perspective view of one preferred embodiment of an apparatus arrangement of the invention, featuring a non-circulating configuration.

FIG. 5 shows an alternative model that does not have a circulating pump 50 and does not circulate liquid 200. This non-circulating embodiment of the invention 1 includes an arrangement for filling the lumen of the endoscope 100 with cleaning solution 200 and a hydrophobic filter 96 for allowing air to escape from the endoscope 100 during filling of the endoscope 100. In the embodiment of FIG. 5, the filling means is a reservoir 30. The reservoir 30 is preferably integrally formed with the bag 10, such as on the side of the bag as shown in FIG. 5. The chamber 32 of the reservoir 30 is preferably pre-filled with cleaning solution 200. The chamber 32 of the reservoir 30 preferably contains about 25-75 cc's of solution 200. This embodiment is simple to operate, eliminates the storing of pumps, and provides recurring revenue in the form of sales of a bag 10 having an integrated and charged reservoir 30. In lieu of an integral reservoir 30 on the bag 10, a separate filling mechanism could be used, such as a separate bag reservoir 30 that gravity feeds into the scope through tubing, or a syringe, or like injection means.

Figure 6:
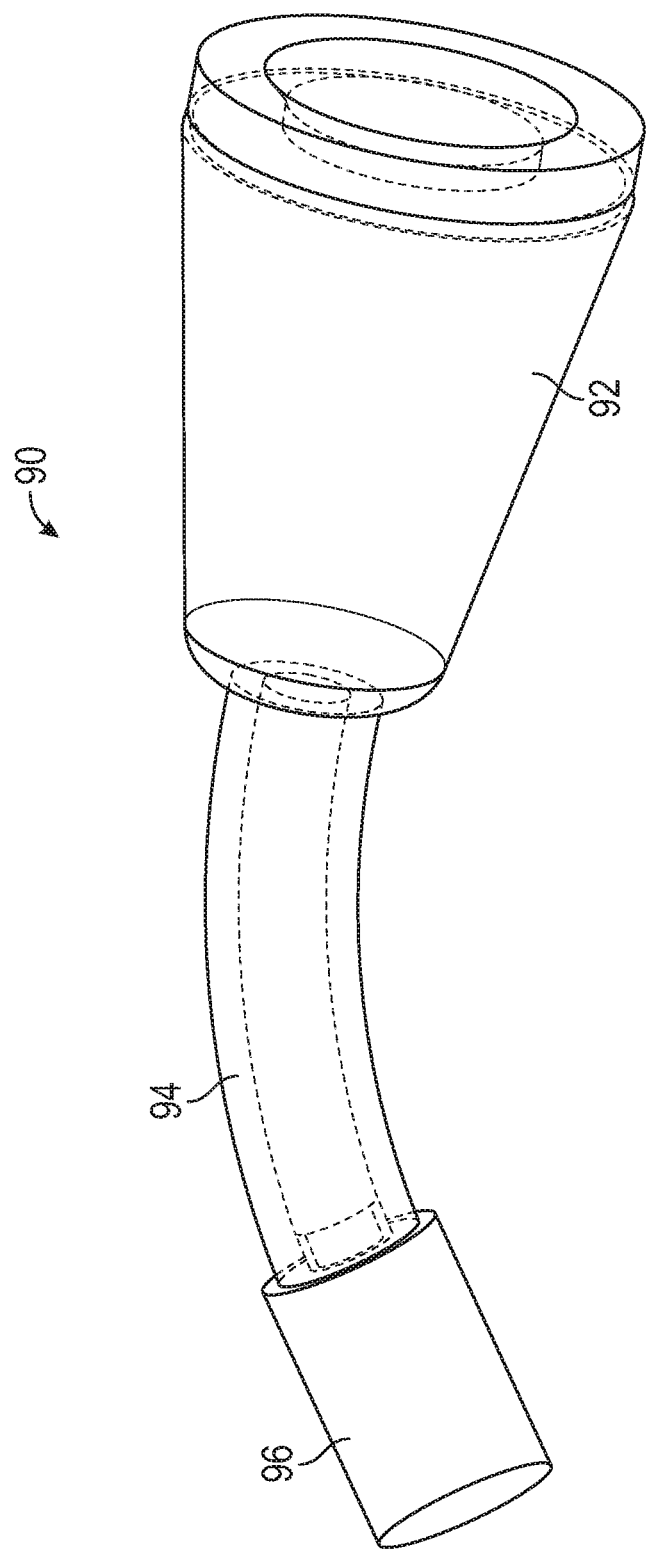
FIG. 6 is a side view of an air eliminating filter for use in a non-circulating embodiment.

FIG. 6 shows an embodiment of a distal end plug 90 assembly for fitting on the distal end 110 of the scope insertion tube 108. The distal end plug 90 is configured to attach to the end of the scope and incorporates an air venting filter 96 to allow escape of air but not liquid. The distal end plug 90 includes a scope input connector 92, a hydrophobic filter 96 on a distal end, and a hose section 94 fluidly connecting the input connector 92 and the filter 96. The hose section 94 is preferably clear, which allows the user to see the liquid coming out and the air escaping; this allows the user to quit pumping cleaning solution 200 once the internal channels or lumen of the endoscope 100 are full. Once no more air comes out, the user knows the lumens are full and can stop the filling process. The hose section 94 is preferably about 2-4 inches long. The input connector 92 is preferably made of a semi-soft polymer, such that the connector 92 sealingly accommodates most sizes of scope geometries. The plug 90 also provides protection for the camera and light located on the distal tip, so they don't get damaged in transport or handling.

In the embodiment of FIG. 5, the user connects the tubing 34 35 36, and 37 to the inlet ports of the endoscope 200 and the distal end plug 90 to the insertion tube 108 of the endoscope 100. Once the openings of the endoscope 100 are connected to the device, the user applies pressure to the reservoir 30 to deliver the cleaning solution 200 to the endoscope 100. The hydrophobic filter 96 allows air but not cleaning solution 200 to escape during filling. Pressure can be applied by compressing the reservoir 30, such by pushing the hand along the reservoir 30, such that cleaning solution 200 is pushed out of the reservoir 30 into the tubes and the lumen of the endoscope 100.

Accessories that might be included or sold with the assembly 1 include a reusable tray, disposable tubing, absorption pad, moist wipes, and a syringe. The assembly of the invention 1 can be provided in the form of a kit. The components of the kit are preferably arranged in a convenient format for assembly prior to use, such as in a surgical tray or case. However, the kit components do not have to be packaged or delivered together, provided that they are assembled or collected together in the operating room for use at the time of surgery.

The apparatus is preferably reusable, due to the anticipated cost of the pump and motor. However, the enzymatic fluid 200 is not reusable. It may be desirable to replace the connecting tubing. Consequently, the associated sale of enzymatic fluid and tubing provides a recurring revenue stream.

Methods of Use

In operation, the invention presents various methods of use for treating an endoscope 100 to prevent adhesion of bioburden on internal walls of a lumen of said endoscope 100.

The invention is designed to provide an additional step between steps 2-3 and 9-10 above, as indicated in new step 3-4 and 9 below:
1. Scope is used in a surgical procedure
2. Scope is pre-cleaned at the point of use
3. Scope is treated at the point-of-use by continual circulation of an enzymatic cleaning solution
4. Scope is contained in a sealable containment/pump device
5. Scope is collected for reprocessing
6. Scope is transported to a cleaning and sterilization facility (typically located in the hospital where the scope was used)
7. Scope is washed
8. Scope is sterilized
9. Scope is contained in a sealable containment/pump device to prevent re-contamination
10. Scope is returned to the point of care in preparation for the next procedure
11. Repeat steps 1-11 after each use The invention 1 provides an apparatus that attaches to an endoscope 100 at the point-of-use. As soon as an endoscopic procedure is complete, the endoscope 100 is hooked up to the circulation apparatus. The apparatus infuses and continuously circulates enzymatic cleaning solution 200 under low pressure within the critical spaces of the lumen of the scope. Continual circulation of enzymatic fluid inside the lumen keeps bio-burden from drying out. Continual circulation also loosens bio-burden particles.

In one preferred method, shortly after use of an endoscope 100 in a medical procedure, cleaning solution 200 is injected into the endoscope 100. The cleaning solution is circulated in in the endoscope 100, whereby circulation of the cleansing solution 200 within the endoscope 100 comprises a treated condition in which the enzymatic fluid 200 prevents adhesion of bioburden on said internal walls of said lumen of said endoscope.

Hookup of the scope 100 to the liquid supply 30 and collection/suction tubing connectors is preferably done entirely outside the containment bag 10 in a dry condition. Once all connections are made, the scope 100 and all tubing and set are placed inside the containment bag 10.

Once the setup is completed, the fluid pathways are opened and the pump 50 is turned on. Fluid 200 begins recirculating per the selected conditions until circulation is stopped and disconnected. Once the tube connections to the scope 100 are removed the scope 100 can be transferred to the disinfection/cleaning and sterilization operation. The entire tubing set 60 70 and fluid path components can be sealed inside the containment bag and red bagged. It comes close to being a closed system.

The bag 10 can be sealed shut and placed bottom side down in a tote/tray/etc.

The endoscope 100 is stored in the treated condition until cleaning of the endoscope 100. The treated condition may involve continuous circulation of cleaning fluid 200, intermittent circulation of cleaning fluid 200, or a soaking condition after an initial period of fluid 200 circulation. During the treated condition, the cleaning solution 200, including preferably enzymes in the cleaning solution 200, prevents bioburden from adhering to walls of internal lumen of the endoscope 100. In some cases, this will involve removal of bioburden from the walls (such as by protein breakdown or detergent action) and in other cases prevention of bioburden from sticking to the walls (such as by maintaining bioburden in solution). When it is time to clean the endoscope 100 for reuse, the treated condition is terminated. The endoscope 100 is then cleaned for reuse in the conventional manner, except that the treated condition facilitates the cleaning of the endoscope by reducing or eliminating residual bio-burden on the internal lumen of the endoscope 100.

Alternatively, the user can elect not to completely fill the lumens. This option may be particularly suited for the embodiment of FIGS. 5-6. Air space may speed up fluid motion in the lumens during agitation of the apparatus 1, such as by periodic manual agitation or mechanical oscillating means.

Although the present invention has been described in terms of specific embodiments, it is anticipated that alterations and modifications thereof will no doubt become apparent to those skilled in the art. It is therefore intended that the following claims be interpreted as covering all alterations and modifications that fall within the true spirit and scope of the invention.

What is claimed is:

1. A device for treating an endoscope after use to prevent adhesion of bioburden on internal walls of a lumen of said endoscope, said endoscope having one or more input ports leading to said lumen, and an insertion tube having a distal end comprising:
    at least one endoscope input member, a trailing end of the at least one endoscope input member configured to selectively attach to at least one of said input ports of said endoscope,
    an endoscope outlet member, a lead end of the endoscope outlet member configured to selectively attach to said distal end of said endoscope insertion tube,
    a cleaning solution,
    a pump, wherein the pump is a hand pump, the pump situated for use in selective circulation of the cleaning solution through the endoscope input member, through said lumen of said endoscope, through said endoscope outlet member, and back into said lumen of said endoscope via the endoscope input member,
    a reservoir, the reservoir configured for storing and retaining the cleaning solution until circulation of the cleaning solution in the device, and
    a leading end of the endoscope input member in fluid communication with the reservoir.

2. The device of claim 1, further comprising an endoscope containment bag sized and configured to receive said endoscope, to thereby protect the endoscope and prevent spilling of the cleaning solution during treatment of the endoscope.

3. The device of claim 2, wherein the endoscope containment bag is selectively sealable.

4. The device claim 1, wherein the cleaning solution is an enzymatic cleaning solution.

\* \* \* \* \*